United States Patent [19]

Walles et al.

[11] Patent Number: 4,756,844

[45] Date of Patent: Jul. 12, 1988

[54] CONTROLLED-RELEASE COMPOSITION HAVING A MEMBRANE COMPRISING SUBMICRON PARTICLES

[75] Inventors: Wilhelm E. Walles, Freeland; Donald L. Tomkinson, Auburn, both of Mich.

[73] Assignee: The Dow Chemical Company, Midland, Mich.

[21] Appl. No.: 947,111

[22] Filed: Dec. 29, 1986

[51] Int. Cl.$^4$ .................. C11D 3/39; C11D 7/18; C11D 17/00; B32B 5/16

[52] U.S. Cl. .................. 252/95; 252/174.13; 252/186.26; 252/186.29; 252/186.32; 252/186.34; 252/186.36; 427/213.3; 427/213.36; 428/402.21; 428/402.22; 428/402.24

[58] Field of Search .............. 252/95, 186.26–187.37, 252/174.13; 428/402.2, 402.21, 402.22, 402.24; 424/31–33; 427/213.3, 213.36, 220, 221

[56] References Cited

U.S. PATENT DOCUMENTS

| | | | |
|---|---|---|---|
| 3,441,507 | 4/1969 | Schlefer et al. | 252/95 |
| 3,459,665 | 8/1969 | Schlefer et al. | 252/95 |
| 3,494,786 | 2/1970 | Nielsen . | |
| 3,494,787 | 2/1970 | Lund et al. | |
| 3,639,285 | 2/1972 | Nielsen | 252/100 |
| 3,645,911 | 2/1972 | van Rosauw et al. | 252/316 |
| 3,666,680 | 5/1972 | Briggs | 252/95 X |
| 3,714,049 | 1/1973 | Charle et al. | 252/90 |
| 3,847,830 | 11/1974 | Williams et al. | 252/186 |
| 3,909,444 | 9/1975 | Anderson et al. | 428/402.24 |
| 3,952,741 | 4/1976 | Baker | 128/260 |
| 3,992,317 | 11/1976 | Brichard et al. | 252/95 X |
| 4,003,841 | 1/1977 | Hachmann et al. | 252/94 |
| 4,094,808 | 6/1978 | Stewart et al. | 252/95 X |
| 4,120,812 | 10/1978 | Lutz | 252/95 X |
| 4,126,573 | 11/1978 | Johnston | 252/99 |
| 4,128,495 | 12/1978 | McCrudden | 8/111 X |
| 4,131,562 | 12/1978 | Lutz et al. | 252/95 X |
| 4,134,850 | 1/1979 | McCrudden et al. | 8/111.5 X |
| 4,136,052 | 1/1979 | Mazzola | 252/94 |
| 4,225,451 | 9/1980 | McCrudden et al. | 252/99 |
| 4,287,135 | 9/1981 | Stober et al. | 260/502 R |
| 4,321,157 | 3/1982 | Harris et al. | 252/174.25 |
| 4,321,301 | 3/1982 | Brichard et al. | 428/403 |
| 4,327,151 | 4/1982 | Mazzola | 428/407 |
| 4,356,109 | 10/1982 | Saeki et al. | 428/402.21 |
| 4,403,994 | 9/1983 | Hignett | 8/111 |
| 4,421,664 | 12/1983 | Anderson et al. | 252/94 |
| 4,421,669 | 12/1983 | Brichard | 252/95 |
| 4,572,869 | 2/1986 | Wismer et al. | 428/402.24 |

*Primary Examiner*—Prince E. Willis
*Attorney, Agent, or Firm*—Barbara J. Sutherland

[57] ABSTRACT

Novel controlled-release compositions are disclosed. These compositions comprise: (1) an agent suitable for use in a selected environment; and (2) a membrane surrounding this agent. The membrane is substantially inert to the agent and permeable to the environment, its thickness and permeability comprising a means for controlling diffusion of the environment therethrough. The membrane thickness is substantially uniform due to the presence of a quantity of submicron particles therein, these particles being substantially inert to the membrane and the agent. The membrane comprising the submicron particles is capable of releasing the agent to the selected environment at a predetermined time by a variety of mechanisms. The release mechanisms that may be selected for use with a composition will depend in part on the choices of agent, membrane, and submicron particle materials, as well as on the choice of environment into which the composition is to be introduced.

**29 Claims, 1 Drawing S

CONTROLLED-RELEASE COMPOSITION HAVING A MEMBRANE COMPRISING SUBMICRON PARTICLES

BACKGROUND OF THE INVENTION

The present invention relates to controlled-release and delayed delivery compositions.

For years manufacturers have sought ways to control the release of certain agents into various selected environments where they are to be introduced. These agents include, for example, medicines, pesticides, herbicides, cosmetics, laundry products, pigments, and many other materials. For these agents a delayed release and/or continuous release is in some cases desirable in order to maximize the agent's effectiveness, minimize or eliminate undesirable effects, or do both.

One of the most effective and currently wide-spread means of achieving the goal of controlled agent release is encapsulation. Encapsulation involves the formation of a protective wall of some type around a small particle, agglomeration of particles, or droplet of agent material. The wall is composed of a material suitable to achieve this goal, the material varying according to the degree of permeability needed, the type of undesirable reactions to be avoided, and any number of other requirements, each of which must be considered to ensure the best wall material choice. The agent and wall materials can together comprise solid and liquid mononuclear structures, emulsion and suspension compositions, and solid/liquid combinations in which a liquid is adsorbed into a porous matrix, as well as polynuclear structures involving solids, liquids, or both, and having more than one wall or agent layer.

To prepare capsules of these types a wide variety of methods and processes have been developed. One method involves the use of fluidized beds. In this process particles of agent material are sprayed with wall material while they are suspended in a gas stream, e.g., air or nitrogen. The wall material sprayed can be of a polymer solution, a molten wax, molten sulfur, an emulsion, a suspension such as a latex, or other material, and is continued until the desired wall thickness is obtained. A design modification called the Wurster column can be employed to reduce particle agglomeration. Both liquids and solids can be encapsulated using the fluidized bed method, with liquids generally requiring absorption into a porous matrix such as clay, freezing and/or drying, or the use of thickening additives either before or during the fluidization and coating steps. Regardless of the method or materials chosen, the goal is to produce a composition capable of controlled agent release, such as release at a predetermined time. This release can be immediate upon introduction into a selected environment, it can be delayed for a specific amount of time, or in the case of a number of agent particles or drops having differing wall thicknesses or compositions, it may be continuous over a period of varying length. The release is effected by varying mechanisms acting on the wall, such as by dissolution by the environment, reaction with the environment, or osmotic diffusion causing rupture of the capsule wall. U.S. Pat. No. 3,952,741, for example, illustrates a controlled delivery system based on osmotic bursting of a water-permeable wall.

These mechanisms are effective for a wide variety of uses. The osmotic rupture mechanism is particularly well-suited to applications where release of the agent is to be delayed for a predetermined amount of time and then effected fairly rapidly. One such application is, for example, in laundry products containing bleaches. Fabric damage can result when the bleach is allowed to dissolve prior to the completion of the washer's filling cycle and the start of the agitation cycle because of local high bleach concentrations. Therefore, in order to prevent the local high concentrations it is desirable to delay bleach release for a few minutes and then effect release rapidly. U.S. Pat. No. 3,992,317 describes an encapsulated composition, applied to peroxygen compounds, that accomplishes this delay. However, while release of a single particle of peroxygen compound may be effected rapidly, a graph of the release of a sampling of a number of particles prepared by the method of this patent shows a range of release times over a significant portion of the total time between introduction into the environment and complete release of all agent. These essentially sequential releases allow for the undesirable local high concentrations, although the concentrations will be somewhat more uniform than when no delay mechanism is used.

Similar problems are encountered when the type of encapsulation described in U.S. Pat. No. 3,992,317 is used for pesticides, herbicides, medicines, pigments, and so forth. Thus, what is needed is a composition and method for increasing the uniformity of release time for a given quantity of agent into a selected environment. The present invention is such a composition and method.

SUMMARY OF THE INVENTION

The present invention includes a composition comprising: (1) an agent suitable for use in a selected environment; and (2) a membrane surrounding this agent, this membrane being substantially inert to the agent and permeable to the environment, the thickness and permeability of the membrane comprising a means for controlling diffusion of the environment therethrough, the membrane further comprising submicron particles that are substantially inert to the membrane and the agent, such that the membrane is capable of releasing the agent to the environment.

The present invention also comprehends a laundry composition comprising an encapsulated bleach combined with a laundering formulation of varying type.

DESCRIPTION OF THE PREFERRED EMBODIMENTS

Figure 1:
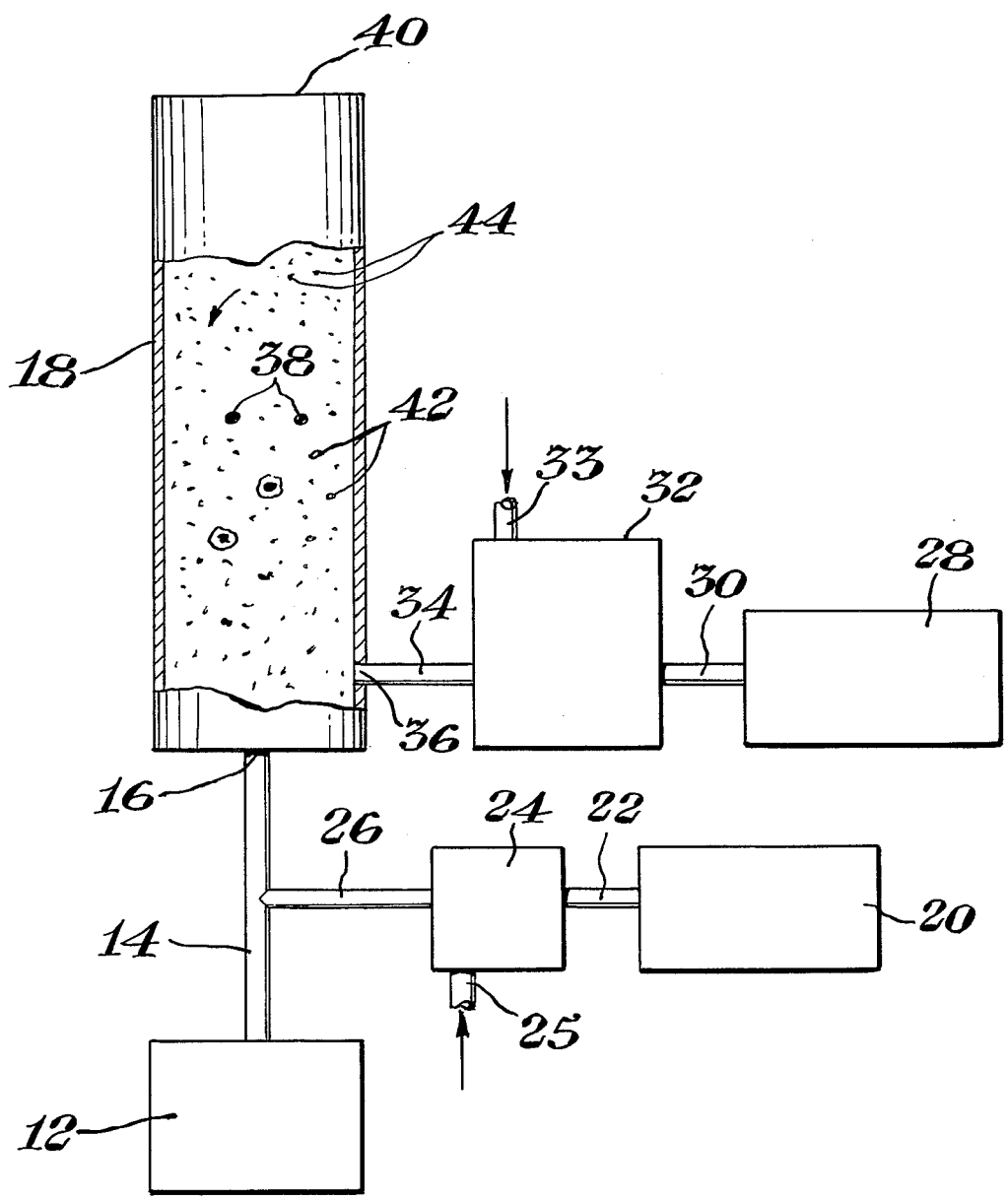
FIG. 1 is a plan view in section of a preferred embodiment of the batch fluidized bed reactor by which the present invention can be prepared.

Accordingly, there is provided an encapsulated composition that allows controlled release of a sampling of any of various types of agent at a narrowly predetermined time.

In general, the present invention is an encapsulated composition comprising an agent that is responsive to a selected environment and is surrounded by a membrane. The membrane is permeable to the environment in which the agent will be used, and the environment diffuses through the membrane until, by one of the mechanisms described below, the membrane ruptures and releases the agent. This membrane has a quantity of an inert compound incorporated into it. The inert compound, called an anti-coalescent, operates to improve the uniformity of application of the membrane, which in turn improves the uniformity and predictability of the release times of a given sampling of agent. The choices of agent, membrane, and anticoalescent materials, as well as the quantities of each, determine the release time in a given environment.

Various release mechanisms are operable in the present invention, and may be individually applicable to a given combination of selected agent, membrane material, and environment, or may be concurrently or even synergistically effected. In one preferred embodiment the release mechanism is that of simple osmotic diffusion, in which the increased volume within the membrane due to the presence of a quantity of the environment material causes rupture of the membrane and concurrent release of the agent to the environment at large. The diffusion of the environment through the permeable membrane, resulting from the osmotic attraction and/or hygroscopicity of the agent, increases the volume enclosed, resulting in distension of the membrane and, eventually, its rupture and resultant release of the agent to the environment. For example, simple salts, such as $CaCl_2$, $KHSO_4$, $Na_2CO_3$ and urea generally attract enough water to rupture a polyvinyl chloride membrane. In another preferred embodiment, the release mechanism requires selection of both agent and environment such that the two will react to liberate a gas. Osmotic diffusion still occurs, and the reaction of this agent and environment results in gas liberation. This in turn results in a hastened distension, and therefore hastened rupture, of the membrane. The presence within the membrane material of a quantity of an inert anticoalescent compound alters the timing and reliability of burst-type release as compared with membranes of similar composition without an anticoalescent, as will be described below.

The agent encapsulated according to the present invention can also be released by a third method, that of crushing. The crushing can be performed by any means of inducing mechanical pressure from the outside of the composition, and can be employed in lieu of diffusion-actuated release mechanisms, or concurrently with these mechanisms. Other release mechanisms are also operable as to the present invention.

The first selection to be made, therefore, is that of agent. The agent can be either liquid or solid. If it is a liquid, it can be absorbed into a porous clay or porous sodium chloride matrix before encapsulation in a membrane. Alternatively, it can be frozen, dried, or mixed with a thickening additive first. In a preferred embodiment of the invention the selected agent is an oxidizing agent, preferably a bleach capable of forming oxygen, chlorine, or a mixture of these. The bleach can include, but is not limited to, ammonium persulfate, potassium persulfate, sodium persulfate, sodium peroxide, sodium chlorite, calcium hypochlorite, chlorinated lime, sodium perborate, sodium hypochlorite, lithium hypochlorite, dichlorodimethylhydantoin, magnesium monoperoxyphthalate hexahydrate, potassium perphosphate, or a number of organic chlorine derivatives such as the chlorocyanurates, including N-chlorocyanuric acid. Liquid bleaches may be used following absorption into porous clay, for example, a 10 percent hydrogen peroxide solution, a 20 percent sodium hypochlorite solution, or a dilute hypochlorous acid solution, each absorbed into the clay. Of these, peroxy compounds and magnesium monoperoxyphthalate hexahydrate are preferred, and magnesium monoperoxyphthalate hexahydrate is more preferred. In selecting the agent it is obvious that the environment should concurrently be considered, and this is the reason behind the preference for oxidizing agents. The environment into which these oxidizing agents are usually introduced is water, and most react with water to liberate oxygen gas. Thus, the present invention can be utilized, in one preferred embodiment, in the field of laundry detergents and laundry detergent additives, in which magnesium monoperoxyphthalate hexahydrate is commonly used as a bleach in an aqueous solution. This compound has among its desirable properties a reduced possibility of fabric damage when compared with some other bleaches and a good activity level at commonly employed washing temperatures.

When the selected agent and environment are thusly reactive, the gas thereby produced is a primary means of release of the agent to the selected environment. As noted, the gas increases in volume as the reaction progresses, distending the membrane surrounding the agent particle until it reaches its maximum elongation or distension. As gas continues to be produced, and environment continues to osmotically diffuse through the membrane, the membrane suddenly bursts and the agent particle or particles are released into the environment at large. Microscopic examination shows that the membrane, no longer continuous but having at least one aperture, is frequently left with a gas bubble in it. This gas bubble causes the membrane to float to the surface of the fluid environment rather than to precipitate, which in some cases may facilitate its removal from the system. Following the release, the agent is then entirely exposed to the environment to achieve its purpose. This novel mechanism, therefore, comprises an environment-actuated, gas-assisted rupture mechanism.

It is important, then, to note that for this mechanism any agent and any environment may be selected as long as they satisfy the proviso that their reaction results in liberation of any gas. Other possible embodiments here include, for example, sodium bicarbonate or ammonium carbonate as the agent in a water environment, and a combination of a carbonate and a solid acid as agent, again in a water environment. Very slightly acidic water and bicarbonate react to form carbon dioxide, as do carbonate and solid acids (e.g., citric acid, malonic acid) in the presence of water. Another agent releasing carbon dioxide is benzoyl peroxide, which is a well-known polymerization catalyst. Agent/environment combinations leading to the release of nitrogen gas are also possible. It is also important to note that the environment may be either a liquid, a gas, or a combination, as in the case of a humid environment.

The choice of agent and environment affects a further choice, that of membrane. The membrane, or wall, will surround one or more parts of a liquid or solid agent. The membrane is selected of a material that satisfies at least four requirements: (1) it must be permeable, to a determinable degree, to the selected environment; (2) it should be substantially nonreactive with both the agent and the environment within the delay time, although it may be a material that will dissolve or disperse after bursting has occurred in some uses; (3) it should not interfere with the agent material after release; and (4) it should provide release of the agent under preselected conditions. If this degree of permeability is precisely measurable, it is possible to predetermine or control release time with great accuracy. Permeability generally is inversely proportional to the thickness of the membrane, so calculations will preferably take the thickness into account along with the known degree of permeability. Where the gas release mechanism will be employed, the elasticity of the membrane should also be taken into account.

In general, the membrane is applied as a coating to the agent, forming a capsule, and can comprise any material, or mixture of materials, meeting the above requirements. Among possible membrane materials are natural latexes, synthetic latexes such as polystyrene latex, styrene-butadiene rubber, neoprene, polyvinyl chloride, polyvinylidene chloride, e.g., a SARAN* suspension, polyvinylidene dichloride, ethylene acrylic acid, e.g., PRIMACOR*, thermoplastic polymers such as polystyrene and polycarbonate, cellulose esters, glycolide/lactide copolymers, polytetrafluoroethylene dispersions, e.g., TEFLON*, and mixtures thereof. (*SARAN and *PRIMACOR are trademarks of the Dow Chemical Company. *TEFLON is a trademark of Du Pont de Nemours, E. I., Company.) Other possible membrane materials include lacquers comprising solvents with dissolved polymeric materials such as cellulose acetate, powder coating materials, cellulose ethers, such as METHOCEL* and ETHOCEL*, starches and chemically modified starch products dissolved or suspended in water, colloidal suspensions such as suspensions of colloidal sulfur and colloidal silica, and gases capable of forming coatings, such as monomeric vapors and plasma generated coatings. (*METHOCEL and *ETHOCEL are trademarks of The Dow Chemical Company.) In a preferred embodiment of the invention, a water-permeable material is selected for the membrane and applied over one or more crystals of an oxidizing bleach for use as a laundry detergent additive. Preferred here would be at least one crystal of magnesium monoperoxyphthalate hexahydrate coated with METHOCEL* or ETHOCEL*. In some cases safety factors should be considered, and may dictate against some membrane choices in view of the agent selected. For example, it has been found that ammonium persulfate encapsulated in equal proportion with SARAN* is thermally unstable above about 60° C.

An important aspect of the present invention is that there is incorporated into the membrane material an amount of at least one compound that is inert to both the agent and membrane matrix material, and which comprises particles having submicron diameters. Thus, the inert compound, which serves as an anticoalescent as will be described below, should be essentially a finely comminuted powder of colloidal-size particles. Preferred here are compounds such as polytetrafluoroethylene and compounds selected from the group of fumed microfibrous inorganics consisting of fumed silica, fumed alumina, fumed magnesia, fumed calcia, fumed carbon (carbon black), and fumed titania. Anticoalescent mixtures of any of these can also be used. Other choices include any organic or inorganic compound which is comminuted to submicron particles and meets the inertness limitation. If organic compounds are selected, polymers of higher molecular weight are preferred because of the relative ease with which these form colloids. Because of cost, aqueous colloidal silica is preferred. One or more of these anticoalescent compounds is added to the membrane material, preferably as an aerosol during the coating process by which the membrane is applied to the agent. Alternatively, some compounds can be incorporated directly into the membrane material prior to application. Particularly well-suited for use in this method is polytetrafluoroethylene and aqueous colloidal silica, which are very effective in conjunction with latex media. The advantage to this method is the greatly enhanced ease in determining accurately the level of the inert anticoalescent relative to the membrane material as a whole. Polytetrafluoroethylene can alternatively be applied in aerosol form.

The membrane and anticoalescent materials can be applied to the selected agent in any of various ways. One preferred method is by fluidization of the agent in one of a variety of types of fluidized bed reactors, while spraying with a solution or suspension of the chosen membrane material or materials from either above or below the fluidized agent. The selected reactor may be of the continuous type, or of the batch type as shown in FIG. 1. In this apparatus heated air, nitrogen, a mixture of these, or other gas from heated gas source 12 passes through gas inlet conduit 14 to gas inlet port 16 and enters the fluidization bed 18. At the same time an anticoalescent from anticoalescent source 20 flows through generator inlet conduit 22 to aerosol generator 24, is mixed with a diluent gas entering through membrane diluent gas inlet 25, and then flows through generator outlet conduit 26 and is mixed with the heated gas in gas inlet conduit 14. Alternatively, the anticoalescent from anticoalescent source 20 may be arranged to flow from aerosol generator 24 directly into heated gas source 12. Also concurrently, membrane material from membrane material source 28 flows through spray pump inlet conduit 30 to spray pump 32, is mixed with diluent gas entering through anticoalescent diluent gas inlet 33, and then is sprayed out through spray pump outlet conduit 34 through spray port 36 into the fluidization bed 18.

The agent particles 38 are introduced into fluidization bed 18 by opening filter 40 at the top of fluidization bed 18. They are fluidized in the anticoalescent-bearing gas stream coming through gas inlet port 16 and subsequently or concurrently are exposed to the membrane material being introduced through spray port 36. Thus, the anticoalescent and spray are applied simultaneously, and droplets of membrane material 42 and anticoalescent 44 collide with and coat the agent particles 38. Heated gas, often containing a substantial moisture content depending on the membrane material used, escapes through filter 40 as it is separated from the fluidized particles and any aerosols not incorporated in a particle coating. Although the figure shows only one spray inlet port, more than one may be used to increase the speed of coating or to apply differing membrane materials sequentially, as for multilayered coatings. The ports may then be arranged according to the order of membrane layers desired.

There are four main advantages to the addition of the anticoalescent to the membrane, whether it is added to the membrane prior to or during the application of the membrane to the agent: (1) the anticoalescent greatly improves the uniformity of the thickness of the membrane obtained by reducing agglomeration of the membrane material during the coating process making the time of release more precisely determinable and further narrowing the time period required for complete release over a given batch; (2) the anticoalescent reduces the amount of membrane material needed, as low as $\frac{1}{3}$ to 1/5 of what would be required for a given release time otherwise; (3) the anticoalescent reduces the amount of time needed to apply a given membrane thickness to as little as ⅛ to 1/5 of the overall time; and (4) the anticoalescent reduces or eliminates agglomeration of the membrane material which can result in fouling of the coating means, e.g., of the fluidization bed. Agglomeration of the membrane material has been found to result in the formation of doublets, triplets, etc., of agent particles within one continuous coating. Following or during the coating process, the doublets, etc., appear to frequently separate, leaving uncoated or less coated portions of the perimeter. These portions alter the time of release of these particular particles, thus often substantially reducing the uniformity and sharpness of release times over a given batch. With the addition of the inert anticoalescent, the number of agglomerated particles is greatly reduced, and the timing of release is therefore both narrower and more precisely predictable.

For example, microscopic examination shows that when a fumed microfibrous inorganic compound is selected, there is a general tendency for it to form bead-strings of about 100 Å diameter. These bead-strings are connected as a microfibrous string network. The microfibrous network does not appear to have any effect on the coagulation of the membrane material, but is still effective in reducing agglomeration by forming a network throughout the interior and exterior of the membrane. Some of the other possible anticoalescents remain in discrete areas within the membrane. Either way, the presence of the anticoalescent in the membrane material and/or on its outer surface substantially reduces the number of doublets, triplets, etc., formed, so the membranes are substantially more uniform within a given batch.

In designing or predicting the release time it is necessary to calculate the quantities of agent, membrane, and anticoalescent materials relative to each other, as well as to take into account the features of each, such as permeability of the membrane material and so forth.

In the present invention the membrane, including both membrane material and the incorporated anticoalescent, can be of any desired thickness such that osmotic diffusion of the environment through it proceeds at a rate that produces either the desired rate of gas liberation or other general volume increase, with the result that the releasing rupture of the membrane is controlled. In a preferred embodiment of the invention, this thickness is within the range of from about 1 μm to about 40 μm, and more preferably within the range of from about 5 μm to about 10 μm. These thicknesses are preferred from a standpoint of convenience and economy. Since the thickness of the membrane is inversely proportional to its permeability, there is also a correlation between membrane thickness and the amount of time to elapse prior to release. This relationship will also vary according to the reactivity between agent and environment and the resultant rate of gas release, in the case of the gas-assisted rupture mechanism.

In order to enable the correct membrane thickness, it is possible to also add thickeners or plasticizers to the selected membrane material or to apply multiple membranes. For example, the addition of a plasticizer such as dioctylphthalate to a polyvinyl chloride coating material may be used to produce a very thin membrane, within the range of about 2 μm and about 5 μm, on a crystal of magnesium monoperoxyphthalate hexahydrate having an uncoated diameter of about 1 mm, i.e., a surface area of about 0.031 $cm^2$. This extremely thin membrane is probably enough to prevent significant diffusion and resultant reaction in a very humid environment, but will allow rapid bleach release upon introduction into an aqueous liquid environment.

Conversely, a membrane thickness of about 10 μm, of the same composition and on the same agent particle, is calculated to result in a delay within the range of about 4½ hours and about 5 hours prior to burst release in an aqueous liquid environment. In general, the agent-to-membrane area ratio should be taken into account in calculating desired membrane thickness, and this is preferably within the range of from about 30:1 to about 3:1, and more preferably from about 10:1 to about 6:1. The diameter of the agent core is preferably within the range of from about 0.04 mm to about 3 mm, and more preferably from about 0.5 mm to about 2.0 mm. The desired membrane thickness is also heavily dependent upon the composition of the environment to which it will be introduced, and factors such as the presence of ions in a liquid environment, expressed as total load of salts and as pH, will be a determining factor also.

The level of inert anticoalescent in the membrane can also vary, and is preferably within the range of from about 0.1 ppm to about 50.000 ppm, more preferably from about 1 ppm to about 5,000 ppm, and most preferably from about 5 ppm to about 50 ppm. When the anticoalescent is to be fed into a fluidized bed coater separately from the membrane material a rate of addition of about 0.1 g/hr per 10 liter reactor volume is preferred, but a range of from about 0.05 g/hr to about 10 g/hr is effective. These rates will generally approximate some of the ppm ranges given above.

In a preferred embodiment the encapsulated bleach described above can, for example, be used as a laundry detergent additive. The encapsulated bleach is admixed with a laundering formulation which preferably does not contain any other bleach but may contain other additives. In this use the bleach particles are substantially prevented from interaction with the detergent particles during storage, especially during periods of high humidity. More importantly, the encapsulation prevents most interaction between the bleach and other common laundry additives, such as enzyme cleaners, both during storage in a humid environment and during the first several minutes after introduction into a wash cycle. This is advantageous because the simultaneous presence of both bleach and enzyme cleaner in the same solution results in the deactivation of the enzyme so that the enzyme cannot significantly augment the cleaning effectiveness of the detergent. However, if the bleach is encapsulated according to the present invention, the enzyme will be free to perform its function for a predetermined amount of time, preferably about 2 to 3 minutes, prior to its deactivation when the bleach is released. The same principle can be applied to fabric whitening agents and fabric softeners. A delay time, preferably of about 5 minutes, will allow the whitener to be substantially adsorbed onto the fabric fibers, which tends to prevent its destruction by the bleach released at the end of this time.

Furthermore, the uniformly-timed release provided by the present invention is particularly well suited to laundry bleaches because it ensures substantially complete bleach release within a time range of about 5 percent to about 20 percent of the total time elapsed between introduction of the bleach into the aqueous solution environment and the completion of bleach release. This is desirable because the bleach concentration is almost immediately and uniformly increased throughout the solution, and therefore there is a markedly reduced likelihood of local high bleach concentrations as compared with some other methods of bleach introduction. Local high bleach concentrations can result in "pin-point spotting" damage to fabrics of various types. With a uniformly-timed release at a predetermined point in the wash cycle, this phenomenon is almost entirely avoidable.

Other applications for this invention are also foreseen and hereby encompassed. For example, the present invention can be effectively used to provide a uniformly-timed release for use in various chemical reactions, through encapsulation of one or more reactants or of a catalyst. In various syntheses it can be an effective way to replenish or regenerate an exhausted catalyst, or a more efficient way to allow for specifically sequential reactions. One example of this is the encapsulation of particles in separate batches, such that differing release times provide continuous activity. Corrosion inhibitors and viscosity breakers can be effectively encapsulated for this purpose. As already noted, fabric softeners, such as fatty acid amines, can also be encapsulated for release at the correct time during a wash cycle.

The following examples are set forth to more fully and clearly illustrate the present invention. They are intended to be, and should be construed as being, merely illustrative and not limitative. Unless otherwise indicated, all parts and percentages are by weight. The experimental work was done using a batch coating method to apply the membranes, but a continuous method can alternatively be used.

EXAMPLE 1

About 300 g of payload crystals of magnesium monoperoxyperphthalate hexahydrate (about 1 mm diameter) was fluidized in a UniGlatt Fluidized Bed Apparatus using a Wurster column. These crystals were then sprayed, from the bottom of the bed up, with a SARAN* latex consisting of about 23.3 percent solids in a water base and using a feed rate of about 15 ml/min. The presence of the Wurster column improved circulation, thereby reducing loss of latex droplets not colliding with agent particles. At the same time fumed silica was fed in as an aerosol at a rate of about 0.1 g/hr to about 1 g/hr per 10 liter reactor volume. A spray nozzle with level setting and air pressure of 3 bars combined with full fluidizing air level was used for the SARAN*, along with an exhaust filter bumping scheme of 5 seconds duration with a 45 second interval. Inlet temperature was 60° C. The residence time of the agent crystals was about 10 minutes. It was calculated that this amount of time would produce a composition having a SARAN* membrane thickness of about 16.5 μm. The release of the bleach agent crystals from the SARAN* latex membranes should occur at about 3 minutes from the time of initial contact with a water environment at about 45° C.

EXAMPLE 2

About 250 g of ammonium persulfate was absorbed into porous clay (about 30 percent ammonium persulfate) and coated with about 322 g of a PRIMACOR* ethylene acrylic acid suspension (about 80.6 g solids). Feed rate for the coating was about 5.4 g/min., and spraying was continued about 60 minutes. Fumed silica served as an anticoalescent and was fed in at a rate of about 0.1 g/hr. The final composition analyzed as about 23 percent by weight of the ammonium persulfate, about 38 percent by weight of the PRIMACOR*, and about 39 percent by weight of the clay. Average release time in 80° C. water was about 7 hours.

EXAMPLE 3

About 300 g of porous clay particles containing ammonium persulfate were coated by the method of Example 1. The ammonium persulfate itself represented about 20 percent by weight. The coating was a 7.8 percent solution of METHOCEL* in water, and about 821 g of this solution, comprising about 64.1 g of solids, was sprayed at the rate of about 8 g/min. for about 103 minutes. At the same time fumed silica was fed in as an aerosol at about 0.1 g/hr. The average release time in 80° C. water was about 100 minutes, and at room temperature it was about 8 hours.

EXAMPLE 4

About 500 g of sodium chloride particles were coated as in Example 1 with about 200 g. of a sulfur and gum arabic mixture (14 percent sulfur) diluted in about 800 g of water. The feed rate for the coating was about 6 g/min. and spraying time totalled about 29 minutes. Fumed silica was used as an anticoalescent and was fed in at a rate of about 0.1 g/hr. The particles showed a release time in 80° C. water of about 18 hours.

EXAMPLE 5

About 300 g of lithium hypochlorite particles was coated as in Example 1 with about 137 g of a SARAN* suspension as characterized in Example 1. Spraying was continued about 23 minutes, at a feed rate of about 5 ml/min, producing a coating of about 14 μm in thickness. Fumed silica was used as an anticoalescent and was fed in at a rate of about 0.1 g/hr. The final composition was analyzed to be about 8 percent by weight of SARAN* and about 92 percent by weight of lithium hypochlorite. The average release time in 45° C. water was about 18 minutes.

EXAMPLE 6

About 300 g of ammonium persulfate was absorbed into porous clay (about 30 percent ammonium persulfate) and coated with the SARAN* suspension of Example 1. The suspension was admixed prior to coating with about 2.8 percent, by weight of SARAN*, of polytetrafluoroethylene, and the mixture was sprayed at about 8.8 g/min, for about 60 minutes. Total coating was about 528 g, or about 132 g of solids. About 80 percent of the sampling had released in an 80° C. water environment after about 25 hours.

EXAMPLE 7

The coated particles of Example 2 are used to make a novel laundry composition by mixing 2 parts of an enzyme presoak powder with 10 parts of a bleach-free laundry detergent and 1 part novel encapsulated bleach. This composition, when added to water, provides about 3 minutes enzyme action time, after which the bleach is released, terminating enzyme activity. Thereafter the bleach continues to be active concurrently with the laundry detergent.

EXAMPLE 8

About 500 g of agent crystals of ammonium persulfate (about 0.5 mm diameter) is fluidized in the UniGlatt Fluidized Bed Apparatus described in Example 1. These crystals are then sprayed, from the top down, with the SARAN* latex described in Example 1, but for a time of about 15 minutes at a flow rate of about 15 ml/min. A fumed alumina aerosol is also fed in at a rate of about 0.5 g/hr per 10 liter reactor volume. It is calculated that this amount of spraying will produce a composition with a membrane thickness of about 24.5 μm. An average bleach release time of about 5 minutes is expected in an aqueous environment at about 45° C.

EXAMPLE 9

About 400 g of agent crystals of lithium hypochlorite (diameter about 2 mm) is fluidized in the UniGlatt Fluidized Bed Apparatus described in Example 1. A SARAN* latex is sprayed, from the bottom up, onto the crystals for about 25 minutes at a flow rate of about 15 ml/min. Fumed titania aerosol is also fed in at a rate of about 0.05 g/hr per 10 liter reactor volume. This is calculated to give a membrane thickness of about 50 μm. The expected release time for the lithium hypochlorite agent is about 7 hours following initial contact with a water environment at about 45° C.

EXAMPLE 10

About 350 g of payload crystals of calcium chloride (diameter about 1.5 mm) is fluidized as described in Example 1. A 25 percent ethylene-acrylic acid copolymer latex admixed with about 2 percent by weight of polytetrafluoroethylene, comprising a 28 percent suspension in water with a surfactant, is sprayed onto the crystals from the top down, for about 15 minutes at a flow rate of about 15 ml/min. This time period is calculated to produce a membrane thickness of about 5 μm. Expected average release time is within the range of about 25 minutes after initial contact with an aqueous environment at about 450° C.

EXAMPLE 11

Following the method of Example 1, about 300 g of payload crystals of ammonium persulfate is coated with a mixture of SARAN* latex comprising about 2 percent polytetrafluoroethylene based on weight of the latex. The polytetrafluoroethylene is admixed with the latex and is thus not in aerosol form. It is calculated that spraying the coating for about 10 minutes at a flow rate of about 15 ml/min. will produce a composition having a membrane thickness of about 16.5 μm. Expected average release time of the bleach payload will occur at about 3 minutes from the time of initial contact with an aqueous environment at about 45° C.

EXAMPLE 12

About 350 g of agent crystals of sodium perborate (diameter about 1.5 mm) is fluidized in the UniGlatt Fluidized Bed Apparatus described in Example 1. The SARAN* latex described in Example 1 is sprayed, from the bottom up, onto the crystals for about 5 minutes at a flow rate of about 15 ml/min. Fumed magnesia aerosol is also fed in at a rate of about 0.75 g/hr per 10 liter reactor volume. This time period is calculated to produce a membrane thickness of about 7.9 μm. Expected average release time is within the range of about 1 and about 2 minutes after initial contact with an aqueous environment at about 45° C.

We claim:
1. A composition comprising:
(1) an agent suitable for use in a selected environment; and
(2) a membrane surrounding the agent, the membrane being substantially inert to the agent and permeable to the environment, the thickness and permeability of the membrane comprising a means for controlling diffusion of the environment therethrough, the membrane further comprising submicron particles that are substantially inert to the membrane and the agent, such that the membrane is capable of releasing the agent to the environment.

2. The composition of claim 1 wherein the environment is aqueous.

3. The composition of claim 1 wherein the agent is a solid particle.

4. The composition of claim 1 wherein the agent is a liquid.

5. The composition of claim 4 wherein the liquid is absorbed into a solid porous particle.

6. The composition of claim 5 wherein the solid porous particle is porous sodium chloride.

7. The composition of claim 1 wherein the agent has a diameter within the range of from about 0.05 mm to about 3 mm.

8. The composition of claim 1 wherein the agent has a diameter within the range of from about 0.5 mm to about 2 mm.

9. The composition of claim 1 wherein said agent reacts with said environment to liberate at least one gas selected from the group consisting of oxygen, hydrogen, carbon dioxide, nitrogen, and mixtures thereof.

10. The composition of claim 1 wherein the agent is an oxidizing agent.

11. The composition of claim 10 wherein the oxidizing agent is a bleach.

12. The composition of claim 1 wherein the bleach is selected from the group consisting of magnesium monoperoxyphthalate hexahydrate, ammonium persulfate, sodium persulfate, potassium persulfate, hydrogen peroxide, sodium hypochlorite, lithium hypochlorite, sodium peroxide, sodium chlorite, calcium hypochlorite, hypochlorous acid, chlorinated lime, sodium perborate, organic chlorine derivatives, potassium perphosphate, and mixtures thereof.

13. The composition of claim 1 wherein the membrane has a thickness within the range of from about 5 μm to about 40 μm.

14. The composition of claim 1 wherein the membrane has a thickness within the range of from about 5 μm to about 25 μm.

15. The composition of claim 1 wherein the membrane comprises a material selected from the group consisting of polystyrene latex, styrene-butadiene rubber, neoprene, polyvinyl chloride, polyvinylidene chloride, polyvinylidene dichloride, ethylene acrylic acid, polystyrene, polycarbonate, cellulose esters, glycolide/lactide copolymers, lacquers, cellulose ethers, starches, chemically modified starch products, colloidal suspensions, monomeric vapor coatings, plasma generated materials, and mixtures thereof.

16. The composition of claim 1 wherein the membrane comprises a latex coating.

17. The composition of claim 1 wherein the submicron particles are selected from the group consisting of aqueous colloidal silica, fumed silica, fumed alumina, fumed magnesia, fumed calcia, fumed carbon, fumed titania, polytetrafluoroethylene, and mixtures thereof.

18. The composition of claim 1 wherein the submicron particles are present in an amount within the range of from about 0.1 ppm to about 50,000 ppm relative to the membrane.

19. The composition of claim 1 wherein the submicron particles are present in an amount within the range of from about 1 ppm to about 5,000 ppm relative to the membrane.

20. The composition of claim 1 wherein the diffusion is osmotic.

21. A fabric laundering composition comprising:
   at least one part of a fabric laundering formulation admixed with at least one part of a composition comprising:
   (1) an oxidizing agent suitable to react with an aqueous environment to liberate a gas; and
   (2) a membrane surrounding the oxidizing agent, the membrane being substantially inert to the agent and permeable to the environment, the thickness and permeability of the membrane comprising a means for controlling diffusion of the environment therethrough to permit reaction of the agent with the environment, the membrane further comprising submicron particles that are substantially inert to the membrane and the oxidizing agent, such that the membrane is capable of releasing the agent to the environment.

22. The composition of claim 21 wherein the laundering formulation comprises a detergent and an enzyme cleaner, a fabric softener, a fabric whitening composition, or a mixture thereof.

23. The composition of claim 21 wherein the oxidizing agent is a bleach selected from the group consisting of magnesium monoperoxyphthalate hexahydrate, ammonium persulfate, sodium persulfate, potassium persulfate, hydrogen peroxide, sodium hypochlorite, lithium hypochlorite, sodium peroxide, sodium chlorite, calcium hypochlorite, hypochlorous acid, chlorinated lime, sodium perborate, organic chlorine derivatives, potassium perphosphate and mixtures thereof.

24. The composition of claim 21 wherein the membrane comprises a material selected from the group consisting of polystyrene latex, styrene butadiene rubber, neoprene, polyvinyl chloride, polyvinylidene chloride, polyvinylidene dichloride, ethylene acrylic acid, polystyrene, polycarbonate, cellulose esters, glycolide/lactide copolymers, lacquers, cellulose ethers, starches, chemically modified starch products, colloidal silica, colloidal sulfur, monomeric vapor coatings, plasma generated materials, and mixtures thereof.

25. A method of producing a controlled release composition comprising:
   (1) selecting an agent suitable for use in a selected environment; and
   (2) surrounding the agent with a membrane, the membrane being substantially inert to the agent and permeable to the environment, the thickness and permeability of the membrane comprising a means for controlling diffusion of the environment therethrough, the membrane further comprising submicron particles that are substantially inert to the membrane and the agent, such that the membrane is capable of releasing the agent to the environment.

26. The method of claim 25 wherein the agent is an oxidizing agent.

27. The method of claim 25 wherein the membrane comprises a latex coating.

28. The method of claim 25 wherein the submicron particles are selected from the group consisting of aqueous colloidal silica, fumed silica, fumed alumina, fumed magnesia, fumed calcia, fumed carbon, fumed titania, polytetrafluoroethylene, and mixtures thereof.

29. In a controlled release composition comprising:
   (1) an agent suitable for use in a selected environment; and
   (2) a membrane surrounding the agent, the membrane being substantially inert to the agent and permeable to the environment, the thickness and permeability of the membrane comprising a means for controlling diffusion of the environment therethrough, such that the membrane is capable of releasing the agent to the environment;
   an improvement comprising the membrane further comprising submicron particles that are substantially inert to the membrane and the agent.

* * * * *